US009238715B2

(12) United States Patent
Chan et al.

(10) Patent No.: US 9,238,715 B2
(45) Date of Patent: Jan. 19, 2016

(54) POLYMERIZABLE COMPOSITION FOR OPHTHALMIC AND MEDICAL USE AND ANTIMICROBIAL COMPOSITION OBTAINED BY POLYMERIZING THE POLYMERIZABLE COMPOSITION

(71) Applicant: NANYANG TECHNOLOGICAL UNIVERSITY, Singapore (SG)

(72) Inventors: Bee Eng Mary Chan, Singapore (SG); Chuncai Zhou, Singapore (SG); Susanna Su Jan Leong, Singapore (SG); Matthew Wook Chang, Singapore (SG); Peng Li, Singapore (SG); Xiaobao Qi, Singapore (SG); Mouad Lamrani, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 13/936,135

(22) Filed: Jul. 5, 2013

(65) Prior Publication Data
US 2014/0163133 A1    Jun. 12, 2014

Related U.S. Application Data

(63) Continuation of application No. 13/700,128, filed as application No. PCT/JP2011/062227 on May 27, 2011, now abandoned.

(30) Foreign Application Priority Data

May 27, 2010    (JP) .................................. 2010-121700

(51) Int. Cl.
*A61L 31/10*    (2006.01)
*C08G 73/02*    (2006.01)
(Continued)

(52) U.S. Cl.
CPC ............. *C08G 73/028* (2013.01); *A61L 27/227* (2013.01); *A61L 27/34* (2013.01); *A61L 27/54* (2013.01); *A61L 2300/404* (2013.01); *A61L 2430/16* (2013.01)

(58) Field of Classification Search
None
See application file for complete search history.

(56) References Cited

U.S. PATENT DOCUMENTS 5,700,559 A * 12/1997 Sheu et al. ................. 428/319.7
5,807,636 A *  9/1998 Sheu et al. .................... 428/403
(Continued)

FOREIGN PATENT DOCUMENTS

DE    102006052342 A1    5/2008
JP         5-501971 A    4/1993
(Continued)

OTHER PUBLICATIONS

J. Biomater. Sci. Polymer Edn. vol. 18, No. 8,—. 1017-1030 (2007), Photopolymerized poly(ethylene glycol) / poly(L-lysine) hydrgels for the delivery of neural progentior cell, Lavik et al.*
(Continued)

*Primary Examiner* — James J Siedleck
*Assistant Examiner* — Peter A Salamon
(74) *Attorney, Agent, or Firm* — Sam K. Tahmassebi; TechLaw LLP

(57) ABSTRACT

An object of the present invention is to provide a polymerizable composition capable of providing antimicrobial properties to ophthalmic and medical devices relatively inexpensively with ease, and an antimicrobial composition obtained by polymerizing the polymerizable composition.
A polymerizable composition for ophthalmic or medical use comprising an epsilon-polylysine having (meth)acryloyl group is provided. The content of the epsilon-polylysine having (meth)acryloyl group in the polymerizable composition is preferably about 0.1 to 99% by weight, based on the whole amount of the composition. A coating agent for ophthalmic or medical use comprising the above polymerizable composition, an antimicrobial composition for ophthalmic or medical use obtained by polymerizing the above polymerizable composition, an ophthalmic or medical device comprising the antimicrobial composition, and a contact lens comprising the antimicrobial composition are also provided.

13 Claims, 5 Drawing Sheets

(51) Int. Cl.
  A61L 27/22  (2006.01)
  A61L 27/34  (2006.01)
  A61L 27/54  (2006.01)

(56) References Cited

U.S. PATENT DOCUMENTS 5,837,377 A * 11/1998 Sheu et al. .................. 428/412
6,454,802 B1 * 9/2002 Bretton et al. ............. 623/6.61
6,733,123 B2 5/2004 Polzhofer et al.

FOREIGN PATENT DOCUMENTS

| JP | H06346000 A | | 12/1994 |
|---|---|---|---|
| JP | 2003335857 A | * | 3/2003 |
| JP | 2003335857 A | | 11/2003 |
| JP | 2006508720 A | | 3/2006 |
| JP | 2010506828 A | | 3/2010 |
| WO | 9103990 A1 | | 4/1991 |
| WO | 2004050132 A2 | | 6/2004 |
| WO | 2008031596 A1 | | 3/2008 |

OTHER PUBLICATIONS

International Search Report and Written Opinion issued in PCT/JP2011/062227 dated Jun. 28, 2011—incl Engl summary.

Bohl and West, Nitric Oxide Producing Materials: A Potential Therapy for Thrombosis and Restenosis. Proceed Int'l Symp Control Rel Bioact Mater.1999;26:56-57.

Bohl and West, Nitric Oxide-Releasing Materials for the Prevention of Thrombosis and Restenosis. Proceed Int'l Symp Control Rel Bioact Mater. 2000;27:143-144.

Gallot and Douy, Comb Copolymers with Thermotropic.and Lyotropic Properties Synthesis and Structural Study. Mol Cryst Liq Cryst. 1987;153:367-373.

Hynes et al., Photopolymerized poly(ethylene glycol)/poly(L-lysine) hydrogels for the delivery of neural progenitor cells. J Biomater Sci Polym Ed. 2007;18(8):1017-1030.

Oliveira and Gehrke, Influence of Network Conformation on Properties of Poly(Amino Acid) Hydrogels. Polymer Preprints, 2000;41(1):745-746.

Percot et al., New hydrogels based on N-isopropylacrylamide copolymers crosslinked with polylysine: membrane immobilization systems. Polymer, Mar. 2000;41(1):7231-7239.

Zhou et al., A photopolymerized antimicrobial hydrogel coating derived from epsilon-poly-L-lysine. Biomaterials. 2011;32:2704-2712.

Extended European Search Report and Written Opinion issued in EP 11786755 dated Jul. 10, 2014.

Zhou et al., A photopolymerized antimicrobial hydrogel coating derived from epsilon-poly-L-lysine. Biomaterials. Apr. 2011; 32(11):2704-2712.

* cited by examiner

POLYMERIZABLE COMPOSITION FOR OPHTHALMIC AND MEDICAL USE AND ANTIMICROBIAL COMPOSITION OBTAINED BY POLYMERIZING THE POLYMERIZABLE COMPOSITION

TECHNICAL FIELD

The present invention relates to a novel epsilon-polylysine having (meth)acryloyl group (hereinafter "(meth)acrylated epsilon-polylysine"), a polymerizable composition for ophthalmic and medical use comprising the (meth)acrylated epsilon-polylysine and other copolymerizable monomers, and an antimicrobial composition for ophthalmic and medical use obtained by polymerizing the polymerizable composition.

BACKGROUND ART

Epsilon-polylysine is widely used as a food additive. Epsilon-polylysine exhibits extensive antimicrobial activity against gram-negative bacteria, gram-positive bacteria, *Escherichia coli* (*E. coli*), *Pseudomonas aeruginosa* (*P. aeruginosa*), *Serratia marcescens* (*S. marcescens*), *Staphylococcus aureus* (*S. aureus*), fungi (e.g., *Candida albicans* (*C. albicans*)), *Fusarium solani* (*F. solani*) and the like, is safe to living organisms and less expensive than other antimicrobial peptides.

Use of such an inexpensive epsilon-polylysine having extensive antimicrobial activity is proposed in various technical fields.

Patent Document 1 (Nippon Paint Co., Ltd.) relates to an antifouling coating composition characterized in that it comprises a polymer containing water-insolubilized polylysine. This document describes using as a binder resin a polylysine-containing water-insolubilized polymer obtained by introducing an unsaturated bond into polylysine and then copolymerizing it with an unsaturated monomer to graft the polylysine to a water-insoluble polymer.

Patent Document 2 (Chisso Corporation) relates to an antimicrobial resin composition and a molded article using the antimicrobial resin composition. This document discloses an antimicrobial resin composition characterized in that it comprises an epsilon-polylysine- or epsilon-polylysine salt-supported filler, and a molded article thereof (e.g., medical and hygienic goods, tableware, products related to daily life, automotive interior materials, household electric appliances, films, sheets, fiber products).

PRIOR ART DOCUMENTS

Patent Documents

PATENT DOCUMENT 1: JP H06-346000 A
PATENT DOCUMENT 2: JP H11-60804 A

SUMMARY OF THE INVENTION

Problem to be Solved by the Invention

An object of the present invention is to provide a polymerizable composition capable of providing antimicrobial properties to ophthalmic and medical devices relatively inexpensively with ease, and an antimicrobial composition obtained by polymerizing the polymerizable composition. Such a polymerizable composition and an antimicrobial composition are useful as, for example, a coating agent for ophthalmic and medical devices.

Means for Solving the Problems

The present invention relates to a polymerizable composition comprising (meth)acrylated epsilon-polylysine, and an antimicrobial composition obtained by polymerizing the polymerizable composition. The polymerizable composition may be used as a coating agent. The antimicrobial composition (for example, antimicrobial hydrogel) has extensive antimicrobial properties for formation of the whole or a part of an ophthalmic or medical device, or for protection and coating of an ophthalmic or medical device. Due to high degree of biocompatibility, antimicrobial property and good wetting characteristics, the polymerizable composition and the antimicrobial composition of the present invention are widely used in many ophthalmic and medical devices, for example, biomedical devices such as contact lenses and bio-implants such as urinary catheters, pacemaker, heart valves, artificial heart, mammary prosthesis, intraocular lenses, wound dressings, artificial organs and delivery carriers for bioactive agents, and total joint replacement.

Specifically, the present invention provides:

[1] A polymerizable composition for ophthalmic or medical use comprising epsilon-polylysine having (meth)acryloyl group.

[2] The polymerizable composition of aspect [1] wherein the content of the epsilon-polylysine having (meth)acryloyl group is about 0.1 to 99% by weight based on the whole amount of the composition.

[3] A coating agent for ophthalmic or medical use comprising the polymerizable composition of aspect [1] or [2].

[4] An antimicrobial composition for ophthalmic or medical use obtained by polymerizing the polymerizable composition of aspect [1] or [2].

[5] An ophthalmic or medical device comprising the antimicrobial composition of aspect [4].

[6] A contact lens comprising the antimicrobial composition of aspect [4].

Advantageous Effects of the Invention

In accordance with the present invention, a polymerizable composition having extensive antimicrobial activity and excellent physical properties and an antimicrobial composition obtained by polymerizing the polymerizable composition are provided relatively inexpensively with ease. The polymerizable composition and the antimicrobial composition are useful as, for example, a coating agent for ophthalmic and medical devices.

Sample A: MA-EPL (X % by weight)-DMA/PEGDA (2/1 weight ratio 100-X % by weight)

Sample B: MA-EPL/DMA (1/10 weight ratio 100-X % by weight)-PEGDA (X % by weight)

Sample C: MA-EPL (X % by weight)-PEG/PEGDA (1/1 weight ratio 100-X % by weight)

Sample D: MA-EPL/PEG (1/5 weight ratio 100-X % by weight)-PEGDA (X % by weight)

Figure 3:
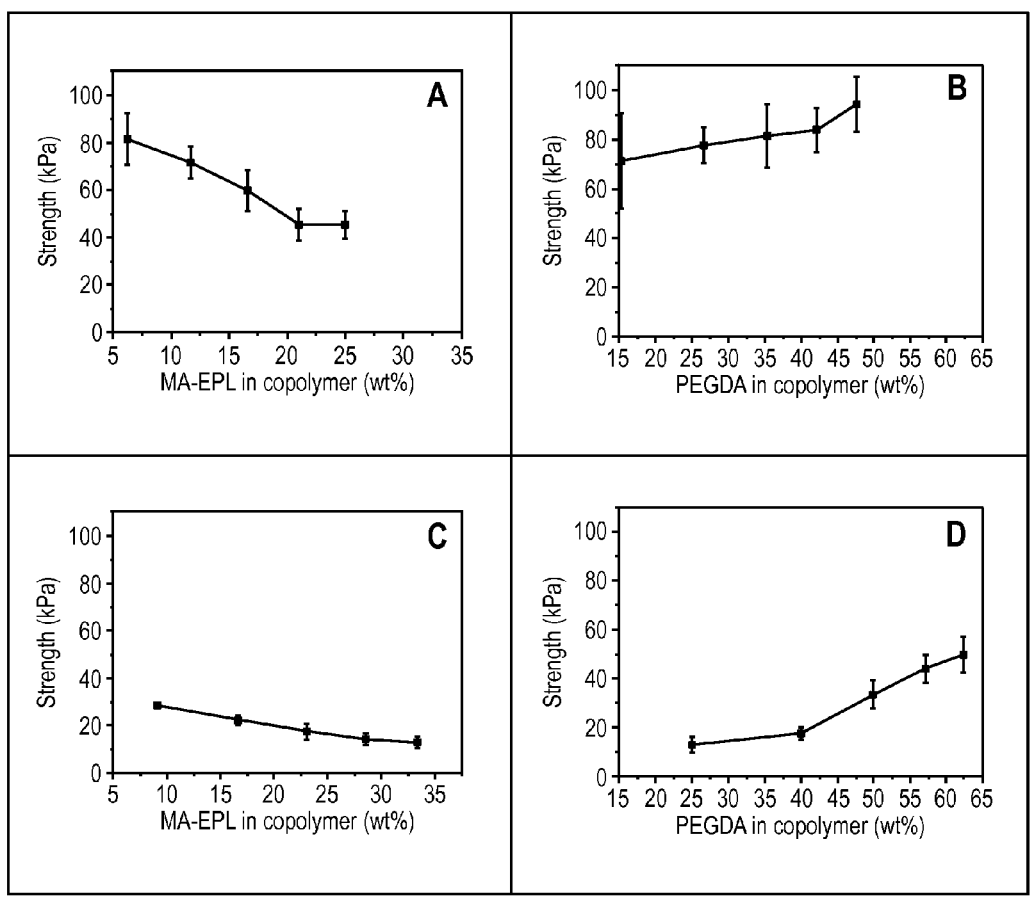

FIG. 3 shows the strengths of the hydrogels of the present invention prepared in the Examples. In the drawing, the vertical axis represents a strength, and the horizontal axis represents a percentage by weight of a component of interest in a copolymer.

Sample A: MA-EPL (X % by weight)-DMA/PEGDA (2/1 weight ratio 100-X % by weight)
Sample B: MA-EPL/DMA (1/10 weight ratio 100-X % by weight)-PEGDA (X % by weight)
Sample C: MA-EPL (X % by weight)-PEG/PEGDA (1/1 weight ratio 100-X % by weight)
Sample D: MA-EPL/PEG (1/5 weight ratio 100-X % by weight)-PEGDA (X % by weight)

Figure 4:
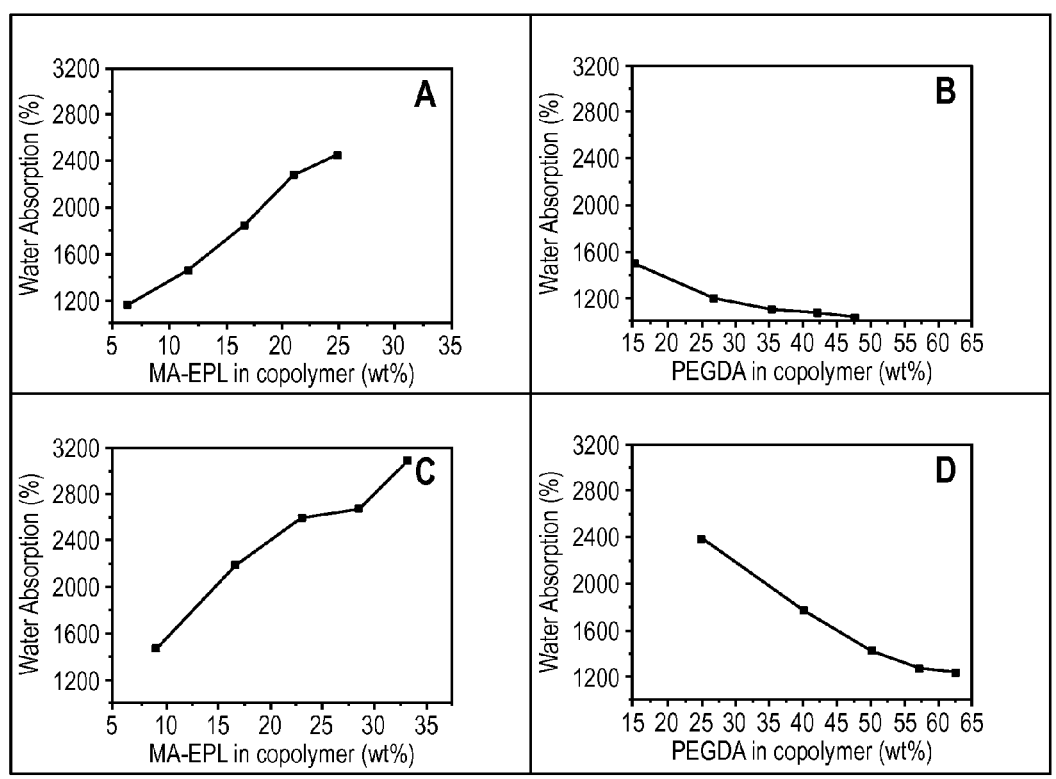

FIG. 4 shows the water absorptions of hydrogels of the present invention prepared in the Examples. In the drawing, the vertical axis represents a water absorption, and the horizontal axis represents a percentage by weight of a component of interest in a copolymer.

Sample A: MA-EPL (X % by weight)-DMA/PEGDA (2/1 weight ratio 100-X % by weight)
Sample B: MA-EPL/DMA (1/10 weight ratio 100-X % by weight)-PEGDA (X % by weight)
Sample C: MA-EPL (X % by weight)-PEG/PEGDA (1/1 weight ratio 100-X % by weight)
Sample D: MA-EPL/PEG (1/5 weight ratio 100-X % by weight)-PEGDA (X % by weight)

Figure 5:
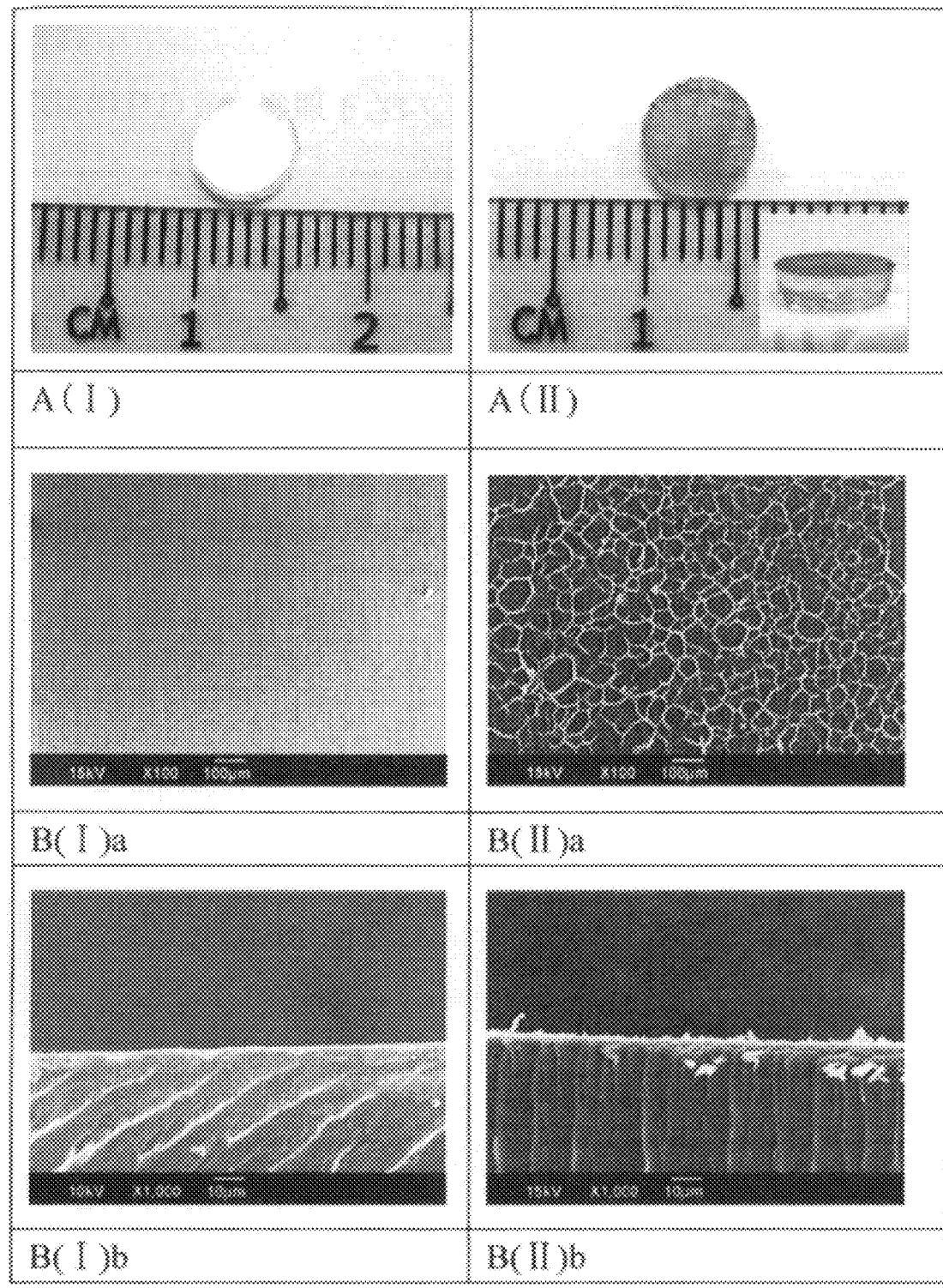

FIG. 5 shows a comparison of a polymer disk (II) coated with a hydrogel of the present invention with a polymer disk (I) without any coating; FIG. 5A shows a photograph of a normal appearance, and FIG. 5B shows scanning electron microscopic (SEM) photographs (Ba shows a photograph of a surface, and Bb shows a photograph of a cross section).

MODES FOR CARRYING OUT THE INVENTION

(Meth)acrylated epsilon-polylysine

It is important that an epsilon-polylysine to be used in the present invention has (meth)acryloyl group in a molecule. The (meth)acryloyl group is firmly bonded to an amino group in a polylysine molecule by covalent bonding via an amide bond to constitute a part of the polylysine molecule. Thus, the epsilon-polylysine to be used in the present invention can be copolymerized with other monomers by use of a C=C double bond of the (meth)acryloyl group, and the epsilon-polylysine can be easily introduced into the resulting copolymer. Antimicrobial compositions suitable for various uses can be provided by appropriately selecting other monomers shown above.

An epsilon-polylysine is a linear chain amino acid homopolymer in which an amino group at the epsilon position of L-lysine forms an amide bond with a carboxyl group. An epsilon-polylysine can be produced biochemically from bacteria, and in view of use as a material for ophthalmic and medical devices, use of such an epsilon-polylysine is preferred in the present invention.

In the present invention, either one of free epsilon-polylysine and epsilon-polylysine salt may be used.

The (meth)acrylated epsilon-polylysine of the present invention can be prepared by, for example, reacting an amino group in an epsilon-polylysine with (meth)acrylic acid or a derivative thereof. For example, it can be prepared by dehydration condensation of an amino group in an epsilon-polylysine with (meth)acrylic acid.

[Polymerizable Composition]

The polymerizable composition of the present invention comprises the (meth)acrylated epsilon-polylysine described above.

The amount of the (meth)acrylated epsilon-polylysine is preferably about 0.1 to 99% by weight, more preferably 1 to 80% by weight, based on the whole amount of the composition.

Examples of other components forming the polymerizable composition include:
(A) a urethane bond-containing monomer;
(B) a hydrophilic monomer;
(C) a silicone monomer other than the compound (A);
(D) an alkyl(meth)acrylate, fluorine-containing alkyl(meth) acrylate, monomer for adjusting hardness; and
(E) a crosslinkable monomer.

With regard to other components shown above for forming the polymerizable composition, examples of components constituting a hydrogel coating agent include (B) and (E) described above, and examples of components to be applied to a contact lens, which is an ophthalmic device, include (A) to (E) described above.

(A) Urethane Bond-Containing Monomer

A urethane bond-containing monomer is a compound having ethylenically unsaturated groups and a polysiloxane structure through a urethane bond (hereinafter, the compound is sometimes referred to as "the compound (A)").

The compound (A) has a bond being an elastic urethane bond and is a component reinforcing without spoiling the flexibility and oxygen permeability of materials by the siloxane segment, imparting stress relaxation to remove brittleness and improving mechanical strength. Further, since the compound (A) has silicone chains in its molecular chain, it can impart high oxygen permeability to a product.

Since the compound (A) has ethylenically unsaturated groups being polymerizable groups at each terminal of the molecule, and is copolymerized with other copolymerization component through the polymerizable group, it has excellent characteristics of imparting to the resulting copolymer not only physical reinforcing effect by intertwisting of molecule but also reinforcing effect by chemical bond (covalent bond).

The compound (A) is a polysiloxane macromonomer in which the polymerizable groups represented by the general formula (1):

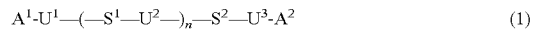
$$A^1-U^1-(-S^1-U^2-)_n-S^2-U^3-A^2 \quad (1)$$

[wherein $A^1$ is a group represented by the general formula (2):

$$Y^{21}-Z^{21}-R^{31}- \quad (2)$$

(wherein $Y^{21}$ indicates a (meth)acryloyl group, a vinyl group or an allyl group, $Z^{21}$ indicates an oxygen atom or a direct bond, and $R^{31}$ indicates a direct bond or an alkylene group having a linear chain, a branched chain or an aromatic ring having 1 to 12 carbons);

$A^2$ is a group represented by the general formula (3):

$$-R^{34}-Z^{22}-Y^{22} \quad (3)$$

(wherein $Y^{22}$ indicates a (meth)acryloyl group, a vinyl group or an allyl group, $Z^{22}$ indicates an oxygen atom or a direct bond, and $R^{34}$ indicates a direct bond or an alkylene group having a linear chain, a branched chain or an aromatic ring having 1 to 12 carbons) (provided that $Y^{21}$ in the general formula (2) and $Y^{22}$ in the general formula (3) may be the same or different);

$U^1$ is a group represented by the general formula (4):

$$-X^{21}-E^{21}-X^{25}-R^{32}- \quad (4)$$

(wherein each of $X^{21}$ and $X^{25}$ is independently selected from a direct bond, an oxygen atom and an alkylene glycol group, and $E^{21}$ is a —NHCO— group (provided that in this case, $X^{21}$ is a direct bond, $X^{25}$ is an oxygen atom or an alkylene glycol group, and $E^{21}$ forms a urethane bond with $X^{25}$), a —CONH— group (provided that in this case, $X^{21}$ is an oxygen atom or an alkylene glycol group, $X^{25}$ is a direct bond, and $E^{21}$ forms a urethane bond with $X^{21}$), or a divalent group derived from diisocyanate selected from the group consisting of a saturated or unsaturated aliphatic group, an alicyclic group and an aromatic group (provided that in this case, each of $X^{21}$ and $X^{25}$ is independently selected from an oxygen atom and an alkylene glycol group, and $E^{21}$ forms two urethane bonds with $X^{21}$ and $X^{25}$), and $R^{32}$ indicates an alkylene group having a linear chain or a branched chain having 1 to 6 carbons);

each of $S^1$ and $S^2$ is independently a group represented by the general formula (5):

[Formula 1]

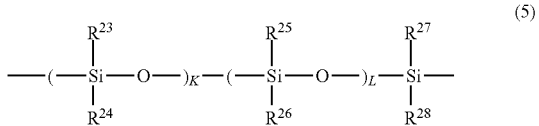

(wherein each of $R^{23}$, $R^{24}$, $R^{25}$, $R^{26}$, $R^{27}$ and $R^{28}$ is independently an alkyl group having 1 to 6 carbons, an alkyl group substituted with fluorine or a phenyl group, K is an integer of 10 to 100, L is 0 or an integer of 1 to 90, and K+L is an integer of 10 to 100);

$U^2$ is a group represented by the general formula (6):

(wherein each of $R^{37}$ and $R^{38}$ is independently an alkylene group having a linear chain or a branched chain having 1 to 6 carbons; each of $X^{27}$ and $X^{28}$ is independently an oxygen atom or an alkylene glycol group; $E^{24}$ is a divalent group derived from diisocyanate selected from the group consisting of a saturated or unsaturated aliphatic group, an alicyclic group and an aromatic group (provided that in this case, $E^{24}$ forms two urethane bonds with $X^{27}$ and $X^{28}$);

$U^3$ is a group represented by the general formula (7):

(wherein $R^{33}$ indicates an alkylene group having a linear chain or a branched chain having 1 to 6 carbons, each of $X^{22}$ and $X^{26}$ is independently selected from a direct bond, an oxygen atom and an alkylene glycol group, and $E^{22}$ is a —NHCO— group (provided that in this case, $X^{22}$ is an oxygen atom or an alkylene glycol group, $X^{26}$ is a direct bond, and $E^{22}$ forms a urethane bond with $X^{22}$), a —CONH— group (provided that in this case, $X^{22}$ is a direct bond, $X^{26}$ is an oxygen atom or an alkylene glycol group, and $E^{22}$ forms a urethane bond with $X^{26}$), or a divalent group derived from diisocyanate selected from the group consisting of a saturated or unsaturated aliphatic group, an alicyclic group, and an aromatic group (provided that in this case, each of $X^{22}$ and $X^{26}$ is independently selected from an oxygen atom and an alkylene glycol group, and $E^{22}$ forms two urethane bonds with $X^{22}$ and $X^{26}$);

n indicates 0 or an integer of 1 to 10], are bound with a siloxane main chain through at least one urethane bond.

In the general formula (1), $A^1$ is a group represented by the general formula (2), as described above:

(wherein $Y^{21}$, $Z^{21}$ and $R^{31}$ are the same as described above), and $A^2$ is a group represented by the general formula (3):

(wherein $Y^{22}$, $Z^{22}$ and $R^{34}$ are the same as described above).

Each of $Y^{21}$ and $Y^{22}$ is a polymerizable group, and a (meth) acryloyl group is particularly preferable from the viewpoint of capable of being easily copolymerizable with the hydrophilic monomer (B).

Each of $Z^{21}$ and $Z^{22}$ is an oxygen atom or a direct bond and an oxygen atom is preferable.

Each of $R^{31}$ and $R^{34}$ is a direct bond or an alkylene group having a linear chain, a branched chain or an aromatic ring having 1 to 12 carbons and an alkylene group having 2 to 4 carbons is preferable.

Each of $U^1$, $U^2$ and $U^3$ represents a group containing a urethane bond in the molecular chain of the compound (A).

In $U^1$ and $U^3$, $E^{21}$ and $E^{22}$ are respectively a —CONH— group, a —NHCO— group, or a divalent group derived from diisocyanate selected from the group consisting of a saturated or unsaturated aliphatic group, an alicyclic group and an aromatic group, as described above. Examples of the divalent group derived from diisocyanate selected from the group consisting of a saturated or unsaturated aliphatic group, an alicyclic group and an aromatic group include divalent groups derived from saturated aliphatic diisocyanate such as ethylene diisocyanate, 1,3-diisocyanate propane and hexamethylene diisocyanate; divalent groups derived from alicyclic diisocyanate such as 1,2-diisocyanatocyclohexane, bis(4-isocyanatocyclohexyl)methane, and isophorone diisocyanate; divalent groups derived from aromatic diisocyanate such as tolylene diisocyanate, and 1,5-diisocyanatonaphthalene; and divalent groups derived from unsaturated aliphatic diisocyanate such as 2,2-diisocyanate diethyl fumarate. Among these, a divalent group derived from hexamethylene diisocyanate, a divalent group derived from tolylene diisocyanate and a divalent group derived from isophorone diisocyanate are preferable because they are comparatively available and strength is easily imparted.

In $U^1$, when $E^{21}$ is a —NHCO— group, $X^{21}$ is a direct bond, $X^{25}$ is an oxygen atom or an alkylene glycol group, and $E^{21}$ forms a urethane bond which is represented by the formula: —NHCOO—, with $X^{25}$. Further, when $E^{21}$ is a —CONH— group, $X^{21}$ is an oxygen atom or an alkylene glycol group, $X^{25}$ is a direct bond, and $E^{21}$ forms a urethane bond which is represented by the formula: —OCONH—, with $X^{21}$. Further, when $E^{21}$ is a divalent group derived from the fore-mentioned diisocyanate, each of $X^{21}$ and $X^{25}$ is independently selected from an oxygen atom and preferably an alkylene glycol group having 1 to 6 carbons, and $E^{21}$ forms two urethane bonds with $X^{21}$ and $X^{25}$. $R^{32}$ is an alkylene group having a linear chain or a branched chain having 1 to 6 carbons.

In $U^2$, $E^{24}$ represents a divalent group derived from diisocyanate selected from the group consisting of a saturated or unsaturated aliphatic group, an alicyclic group and an aromatic group, as described above. Hereto, examples of the divalent group derived from diisocyanate selected from the group consisting of a saturated or unsaturated aliphatic group, an alicyclic group and an aromatic group include divalent groups which are similar to in the fore-mentioned $U^1$ and $U^3$. Among these, a divalent group derived from hexamethylene diisocyanate, a divalent group derived from tolylene diisocyanate and a divalent group derived from isophorone diisocyanate are preferable because they are comparatively available and strength is easily imparted. Further, $E^{24}$ forms two urethane bonds with $X^{27}$ and $X^{28}$. Each of $X^{27}$ and $X^{28}$ is independently an oxygen atom or preferably an alkylene glycol group having 1 to 6 carbons, and each of $R^{37}$ and $R^{38}$ is independently an alkylene group having a linear chain or a branched chain having 1 to 6 carbons.

In $U^3$, $R^{33}$ is an alkylene group having a linear chain or a branched chain having 1 to 6 carbons. When $E^{22}$ is a —NHCO— group, $X^{22}$ is an oxygen atom or an alkylene glycol group, $X^{26}$ is a direct bond, and $E^{22}$ forms a urethane bond which is represented by the formula: —NHCOO—, with $X^{22}$. Further, when $E^{22}$ is a —CONH— group, $X^{22}$ is a direct bond, $X^{26}$ is an oxygen atom or an alkylene glycol group, and $E^{22}$ forms a urethane bond which is represented by the formula: —OCONH—, with $X^{26}$. Further, when $E^{22}$ is a divalent group derived from the fore-mentioned diisocyanate, each of $X^{22}$ and $X^{26}$ is independently selected from an oxygen atom or preferably an alkylene glycol group having 1 to 6 carbons, and $E^{22}$ forms two urethane bonds with $X^{22}$ and $X^{26}$.

Hereto, the examples of alkylene glycol having preferably 1 to 20 carbons in the fore-mentioned $X^{21}$, $X^{25}$, $X^{27}$, $X^{28}$, $X^{22}$ and $X^{26}$ include a group represented by the general formula (8) and the like:

$$-O-(C_xH_{2x}-O)_y- \tag{8}$$

(wherein x indicates an integer of 1 to 4, and y indicates an integer of 1 to 5).

Each of $S^1$ and $S^2$ is a group represented by the general formula (5), as described above.

In the general formula (5), each of $R^{23}$, $R^{24}$, $R^{25}$, $R^{26}$, $R^{27}$ and $R^{28}$ is independently an alkyl group having 1 to 6 carbons, an alkyl group substituted with fluorine, or a phenyl group, as described above.

An example of the alkyl group substituted with fluorine is a group represented by  (m=1 to 10, n=1 to 10), and its specific examples include, for example, side chain alkyl groups substituted with fluorine such as a 3,3,3-trifluoro-n-propyl group, a 2-(perfluorobutyl)ethyl group and 2-(perfluorooctyl)ethyl group; and branched chain alkyl groups substituted with fluorine such as a 2-(perfluoro-5-methylhexyl)ethyl group. Further, in the present invention, when the compound (A) having such an alkyl group substituted with fluorine is used and its content is increased, the lipid-deposit resistance of the ocular lens material obtained tends to be improved.

Further, K is an integer of 10 to 100 and L is 0 or an integer of 1 to 90. K+L is preferably an integer of 10 to 100 and more preferably 10 to 80. When K+L is larger than 100, the molecular weight of the compound (A) is enlarged, its solubility to a pyrrolidone derivative and a hydrophilic monomer other than this is deteriorated, they are not homogeneously dissolved at mixing, and phase separation occurs at polymerization to be opaque; therefore, a homogeneous and transparent ocular lens material tends to be not obtained. Further, when K+L is less than 10, the oxygen permeability of the ocular lens material obtained is lowered and its flexibility tends to be lowered.

Further, n is preferably 0 or an integer of 1 to 10. When n is larger than 10, the molecular weight of the compound (A) is enlarged, its solubility with a pyrrolidone derivative and a hydrophilic monomer other than this is deteriorated, they are not homogeneously dissolved at mixing, and phase separation occurs at polymerization to be opaque; therefore, a homogeneous and transparent ocular lens material tends not to be obtained. The symbol n is more preferably 0 or an integer of 1 to 5.

Further, the compound (A) is a polysiloxane macromonomer in which the polymerizable groups represented by the general formula (9):

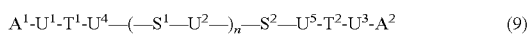

(wherein $A^1$, $A^2$, $U^1$, $U^2$, $U^3$, $S^1$, $S^2$ and n are the same as in the general formula (1), and $U^4$ and $U^5$ are respectively the same as $U^1$ and $U^3$. Provided that $Y^{21}$ and $Y^{22}$ in $A^1$ and $A^2$ are a (meth)acryloyl group, a vinyl group or an allyl group.)

$T^1$ and $T^2$ are a hydrophilic polymer-containing segment or hydrophilic oligomer-containing segment represented by the general formula (10):

(wherein D is a hydrogen atom, a methyl group, or a hydroxy group, Q is a direct bond or an oxygen atom, and n is 5 to 10,000), or the general formula (11):

((wherein M indicates a hydrophilic monomer unit selected from 1,3-methylmethylene pyrrolidone, N-vinylpyrrolidone, (meth)acrylic acid, (meth)acrylic acid salt, N,N-dimethylacrylamide, N,N-diethylacrylamide, 2-hydroxyethyl(meth)acrylate, tetrahydrofuran, oxetane, oxazoline, 2-methacryloyloxyethyl phosphoryl choline and the like, and a polymerization chain of a polymer composed by these units may be a linear chain or a branched chain and may be random or block. X is 5 to 10,000)) are bound with a siloxane main chain through at least one urethane bond.

The compound (A) may further have a hydrophilic polymer structure. The solubility of the compound (A) with a hydrophilic monomer is improved by the structure, and the wettability of a material comprising these can be improved. The structure of the hydrophilic polymer unit includes at least one polymer obtained by polymerizing a zwitter ionic group-containing monomer, such as polyethylene glycol, polypropylene glycol, polyvinyl alcohol, polyvinylpyrrolidone, poly (meth)acrylic acid, poly(meth)acrylate, poly(2-hydroxyethyl (meth)acrylate), polytetrahydrofuran, polyoxetane, polyoxazoline, polydimethyl acrylamide, polydimethylacrylamide and poly(2-methacryloyloxyethyl phosphoryl choline. The molecular weight of the hydrophilic polymer structural unit is 100 to 1,000,000 and preferably 1,000 to 500,000. When the molecular weight is less than 100, hydrophilicity enough for dissolving the compound (A) in a hydrophilic monomer tends to be unable to be imparted. On the other hand, when the molecular weight exceeds 1,000,000, both of hydrophilic domain and hydrophobic domain are enlarged and a transparent material tends not to be obtained.

Typical examples of the compound (A) include, for example, a compound represented by the formula (hereinafter, referred to as the compound (A-1)):

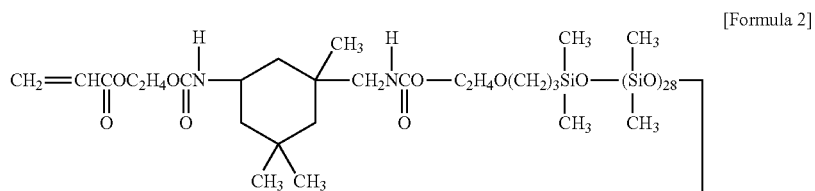

[Formula 2]

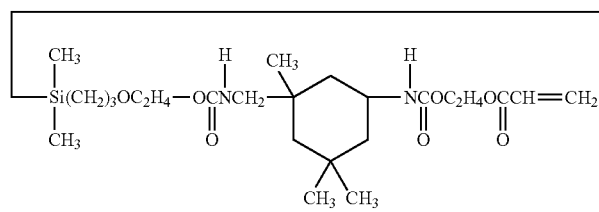

and a compound represented by the formula (hereinafter, referred to as the compound (A-2)):

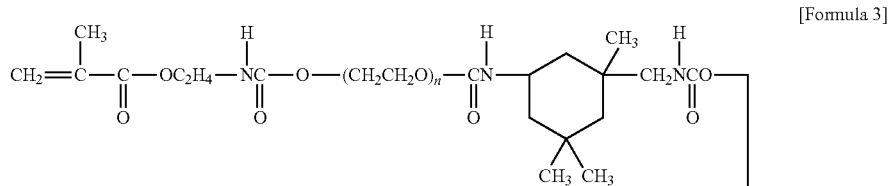

[Formula 3]

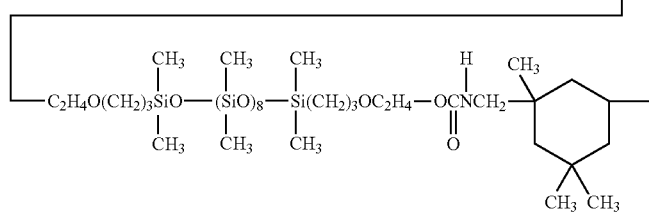

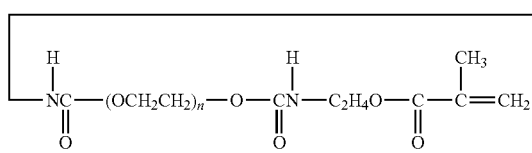

(wherein n is 0 to 10). These can be used alone or a mixture of two or more of these compounds can be used.

The amount of the compound (A) to be used is preferably 1 to 80% by weight based on the total polymerizable components and more preferably 5 to 60% by weight.

(B) Hydrophilic Monomer

It functions as the solubilizer of the silicone component, and is an important component for obtaining a homogeneous material superior in transparency. When the hydrophilic monomer (B) content is increased, excellent surface wettability and lubricity/easy wetting property of surface can be imparted to an ocular lens copolymeric material obtained.

Examples of the hydrophilic monomer (B) include N-vinylpyrrolidone, hydroxyethyl(meth)acrylate, hydroxypropyl (meth)acrylate, hydroxybutyl(meth)acrylate, polyethyleneglycol mono(meth)acrylate, polypropyleneglycol mono(meth)acrylate, N,N-dimethylacrylamide (DMA), N,N-diethylacrylamide, N-(2-hydroxyethyl) acrylamide, N-isopropylacrylamide, acryloylmorpholine, 1-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone and the like, but is not limited to these. These can be used alone or two or more of these can be used in combination. The hydrophilic monomer (B) is preferably 5 to 60% by weight based on the total polymerizable components and more preferably 10 to 55% by weight. When the use amount of (B) is less than 5% by weight, desired wettability and surface lubricity/easy wetting property of surface cannot be achieved and the wettability of material surface tends to be inferior. On the other hand, when it exceeds 60% by weight, oxygen permeability is dominated by water content, and adequate oxygen tends not to be supplied to the cornea considering the wearing state at continuous wearing, at short sleep, or the like.

In order to further improve the oxygen permeability of an obtained ocular lens material and impart flexibility, a silicone monomer (C) other than the fore-mentioned compound (A) is preferably contained as an ocular lens material.

The silicone monomer (C) includes silicone-containing alkyl(meth)acrylate, silicone-containing styrene derivative and diesters of silicone-containing fumaric acid. These can be used alone or two or more of these compounds can be used in combination.

Further, " . . . (meth)acrylate" as referred to herein means " . . . acrylate and/or . . . methacrylate," and the same applies to other (meth)acrylate derivatives.

Examples of the silicone-containing alkyl(meth)acrylate include trimethylsiloxydimethylsilylmethyl(meth)acrylate, trimethylsiloxydimethylsilylpropyl(meth)acrylate, methylbis(trimethylsiloxy)silylpropyl(meth)acrylate, tris(trimethylsiloxy) silylpropyl(meth)acrylate, mono[methylbis(trimethylsiloxy)siloxy]bis(trimethylsiloxy)silylpropyl(meth)acrylate, tris[methylbis(trimethylsiloxy)siloxy]silylpropyl(meth)acrylate, tris(trimethylsiloxy)silyl(propylglycerol)(meth)acrylate, and polydimethylsiloxane di(meth)acrylate and the like. Examples of the silicone-containing styrene derivative include a compound represented by the general formula (12):

[Formula 4]

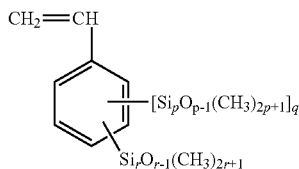

(12)

(wherein p indicates an integer of 1 to 15, q indicates 0 or 1, and r indicates an integer of 1 to 15). In the silicone-containing styrene derivative represented by the general formula (12), when p or r is an integer of 16 or more, purification and synthesis are difficult and the hardness of the ocular lens material obtained tends to be lowered. Further, when q is an integer of 2 or more, synthesis of the silicone-containing styrene derivative tends to be difficult.

Examples of the fore-mentioned silicone-containing styrene derivative represented by the general formula (12) include tris(trimethylsiloxy)silylstyrene, bis(trimethylsiloxy)methylsilylstyrene, (trimethylsiloxy)dimethylsilylstyrene, tris(trimethylsiloxy)siloxydimethylsilylstyrene and the like. Examples of the silicone-containing fumaric acid diester include a compound represented by the general formula (13):

[Formula 5]

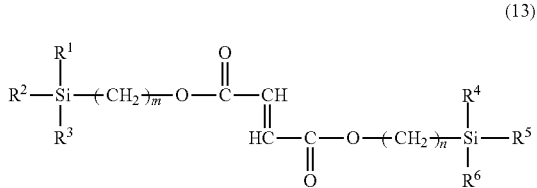

(13)

(wherein each of $R^1$, $R^2$, $R^3$, $R^4$, $R^5$ and $R^6$ independently indicates a methyl group, a trimethylsiloxy group represented by the formula:

[Formula 6]

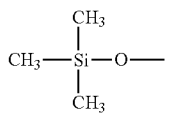

and each of m and n independently indicates an integer of 1 to 3) and the like.

Examples of the fore-mentioned compound represented by the general formula (13) include bis(3-(trimethylsilyl)propyl)fumarate, bis(3-(pentamethyldisiloxanyl)propyl)fumarate, bis(3-(1,3,3,3-tetramethyl-1-(trimethylsilyl)oxy)disiloxanyl)propyl)fumarate, bis(tris(trimethylsiloxy) silylpropyl)fumarate and the like. These can be used alone or a mixture of two or more of these compounds can be used.

Among these, the silicone-containing alkyl(meth)acrylate is preferable from the viewpoints of imparting the flexibility to a material and the copolymerizability with the compound (A) and the hydrophilic monomer (B), and tris(trimethylsiloxy)silylpropyl(meth)acrylate, tris(trimethylsiloxy)silyl(propylglycerol)mono(meth)acrylate, and polydimethylsiloxane di(meth)acrylate are more preferable from the viewpoints of imparting the polymerizability, oxygen permeability and flexibility.

The use amount of the silicone-containing alkyl(meth)acrylate among the silicone monomer (C) is preferably 3 to 80% by weight based on the total polymerizable components, and more preferably 5 to 65% by weight. When the use amount of the silicone-containing alkyl(meth)acrylate is less than 3% by weight, the ocular lens material obtained is highly elastic and brittle and tends to be inferior in flexibility. On the other hand, when it exceeds 80% by weight, the modulus is lowered but the repulsive property is inferior and the surface adhesion property tends to be increased.

The use amount of the silicone-containing styrene derivative among the silicone monomer (C) is preferably 1 to 30% by weight based on the total polymerizable components and more preferably 3 to 20% by weight. When the use amount of the silicone-containing styrene derivative is less than 1% by weight, the oxygen permeability and mechanical strength of the ocular lens material obtained tend to be unable to be adequately improved. On the other hand, when it exceeds 30% by weight, the flexibility of the ocular lens material obtained tends to be lowered.

The use amount of the silicone-containing fumaric acid diester among the silicone monomer (C) is preferably 1 to 50% by weight based on the total polymerizable components and more preferably 3 to 40% by weight. When the use amount of the silicone-containing fumaric acid diester is less than 1% by weight, the oxygen permeability of the ocular lens material obtained tends to be unable to be adequately improved. On the other hand, when it exceeds 50% by weight, adequate mechanical strength tends not to be obtained.

Further, (D) alkyl(meth)acrylate, fluorine-containing alkyl (meth)acrylate and a monomer for adjusting hardness can be used to impart the more desired property of the obtained ocular lens material.

Alkyl(meth)acrylate is a component for adjusting the hardness of the ocular lens material to impart hardness and softness.

Examples of the alkyl(meth)acrylate include linear, branched or cyclic alkyl(meth)acrylate such as methyl(meth)acrylate, ethyl(meth)acrylate, isopropyl(meth)acrylate, n-propyl(meth)acrylate, isobutyl(meth)acrylate, n-butyl (meth)acrylate, 2-ethylhexyl(meth)acrylate, n-octyl(meth)acrylate, n-decyl(meth)acrylate, n-dodecyl(meth)acrylate, t-butyl(meth)acrylate, pentyl(meth)acrylate, t-pentyl(meth)acrylate, hexyl(meth)acrylate, heptyl(meth)acrylate, nonyl (meth)acrylate, stearyl(meth)acrylate, cyclopentyl(meth) acrylate and cyclohexyl(meth)acrylate. These can be used alone or a mixture of two or more of these compounds can be used.

Fluorine-containing alkyl(meth)acrylate is a component for improving the lipid-deposit resistance of the ocular lens material.

Examples of the fluorine-containing alkyl(meth)acrylate include compounds represented by the general formula (14):

$$CH_2=CR^4COOC_sH_{(2s-t+1)}F_t \qquad (14)$$

(wherein $R^4$ indicates a hydrogen atom or $CH_3$, s indicates an integer of 1 to 15, and t indicates an integer of 1 to (2s+1)).

Specific examples of the compounds represented by the general formula (14) include, for example, 2,2,2-trifluoroethyl(meth)acrylate,
2,2,3,3-tetrafluoropropyl(meth)acrylate,
2,2,3,3-tetrafluoro-t-pentyl(meth)acrylate,
2,2,3,4,4,4-hexafluorobutyl(meth)acrylate,
2,2,3,4,4,4-hexafluoro-t-hexyl(meth)acrylate,
2,3,4,5,5,5-hexafluoro-2,4-bis(trifluoromethyl)pentyl(meth)acrylate,
2,2,3,3,4,4-hexafluorobutyl(meth)acrylate,
2,2,2',2',2'-hexafluoroisopropyl(meth)acrylate,
2,2,3,3,4,4,4-heptafluorobutyl(meth)acrylate,
2,2,3,3,4,4,5,5-octafluoropentyl(meth)acrylate,
2,2,3,3,4,4,5,5-nonafluoropentyl(meth)acrylate,
2,2,3,3,4,4,5,5,6,6,7,7-dodecafluoroheptyl(meth)acrylate,
3,3,4,4,5,5,6,6,7,7,8,8-dodecafluorooctyl(meth)acrylate,
3,3,4,4,5,5,6,6,7,7,8,8,8-tridecafluorooctyl(meth)acrylate,
2,2,3,3,4,4,5,5,6,6,7,7,7-tridecafluoroheptyl(meth)acrylate,
3,3,4,4,5,5,6,6,7,7,8,8,9,9,10,10-hexadecafluorodecyl(meth)acrylate,
3,3,4,4,5,5,6,6,7,7,8,8,9,9,10,10,10-heptadecafluorodecyl(meth)acrylate,
3,3,4,4,5,5,6,6,7,7,8,8,9,9,10,10,11,11-octadecafluoroundecyl(meth)acrylate,
3,3,4,4,5,5,6,6,7,7,8,8,9,9,10,10,11,11,11-nonadecafluoroundecyl(meth)acrylate, and
3,3,4,4,5,5,6,6,7,7,8,8,9,9,10,10,11,11,12,12-eicosafluorododecyl(meth)acrylate.

These can be used alone or a mixture of two or more of these compounds can be used.

The contents of the alkyl(meth)acrylate and fluorine-containing alkyl(meth)acrylate are preferably at most 20% by weight based on the total polymerizable components and more preferably at most 10% by weight so that the effect of polymerization components such as the compound (A) and the hydrophilic monomer (B), further, the silicone monomer (C) and the crosslinkable monomer (E) is adequately produced. Further, the contents are at least 0.01% by weight based on the fore-mentioned components and preferably at least 0.1% by weight in order to adequately produce the effect of the alkyl(meth)acrylate and the fluorine-containing alkyl(meth)acrylate.

The monomer for adjusting hardness is a component adjusting the hardness of the copolymer and imparting hardness and softness.

Examples of the monomer for adjusting hardness include alkoxyalkyl(meth)acrylate such as 2-ethoxyethyl(meth)acrylate, 3-ethoxypropyl(meth)acrylate, 2-methoxyethyl(meth)acrylate and 3-methoxypropyl(meth)acrylate; alkylthio alkyl(meth)acrylate such as ethylthioethyl(meth)acrylate and methylthioethyl(meth)acrylate; styrene; alpha-methylstyrene; alkyl styrene such as methylstyrene, ethylstyrene, propylstyrene, butylstyrene, t-butylstyrene, isobutylstyrene and pentylstyrene; alkyl-alpha-methylstyrene such as methyl-alpha-methylstyrene, ethyl-alpha-methylstyrene, propyl-alpha-methylstyrene, butyl-alpha-methylstyrene, t-butyl-alpha-methylstyrene, isobutyl-alpha-methylstyrene and pentyl-alpha-methylstyrene; and the like. These can be used alone or a mixture of two or more of these compounds can be used.

The content of the monomer for adjusting hardness in the polymerizable components is at least 1% by weight and preferably at least 3% by weight in order to adequately impart desired hardness and softness to the ocular lens material. Further, the content is at most 30% by weight and preferably at most 20% by weight in order not to lower the oxygen permeability and mechanical strength of the ocular lens material.

(E) Crosslinkable Monomer

The crosslinkable monomer (E) for adjusting the flexibility and hardness of the material can be added.

Examples of the crosslinkable monomer (E) include allyl(meth)acrylate, vinyl(meth)acrylate, 4-vinylbenzyl(meth)acrylate, 3-vinylbenzyl(meth)acrylate, methacryloyloxyethyl acrylate, ethyleneglycol di(meth)acrylate, diethyleneglycol di(meth)acrylate, diethyleneglycol diallyl ether, polyethyleneglycol di(meth)acrylate such as triethyleneglycol dimethacrylate and tetraethyleneglycol di(meth)acrylate; polypropyleneglycol di(meth)acrylate such as propyleneglycol di(meth)acrylate and dipropyleneglycol dimethacrylate, butanediol dimethacrylate, trimethylolpropane trimethacrylate, and the like. These can be used alone or a mixture of two or more of these compounds can be used.

The content of the crosslinkable monomer (E) is at most one part based on 100 parts by weight (hereinafter, referred to as part) of the total amount of the polymerizable components other than the crosslinkable monomer and preferably at most 0.8 part so that the copolymer is not brittle. Further, the content is at least 0.05 part based on 100 parts of the total amount of the polymerizable components other than the crosslinkable monomer and preferably at least 0.1 part, in order to improve the mechanical strength of the ocular lens material and adequately produce the effect of imparting durability.

When the crosslinkable monomer (E) is used, the compound (A) and the crosslinkable monomer (E) are simultaneously used as crosslinkable components; therefore, the copolymerizability of the ocular lens material is remarkably improved and the various physical properties of the ocular lens material obtained can be improved.

(F) Other Components

A coloring agent, a UV absorber and the like may be appropriately added to the polymerizable composition according to a desired use.

The amount of a coloring agent and a UV absorber to be used is preferably 3 parts or smaller, more preferably 0.01 to 2 parts, based on the total amount of the polymerizable components, which is 100 parts. When the amount exceeds 3 parts, the mechanical strength and the like of the copolymer tend to decrease. Furthermore, in view of the toxicity of a UV absorber and a pigment, such a polymerizable composition may not be suitable for use in a material or device that is to be in direct contact with biotissue. In a case of using an excessive amount of, especially, a pigment, the resulting lens has darker color with lower transparency and is less likely to transmit visible light beams.

[Antimicrobial Composition]

An antimicrobial composition is obtained by polymerizing the fore-mentioned polymerizable composition.

An antimicrobial composition can be prepared, for example, according to the following procedure.

A mixed solution of (meth)acrylated epsilon-polylysine of the present invention and other monomer components described above is appropriately diluted with water, and the mixed solution is irradiated with UV light and/or heated to obtain a desired antimicrobial composition. The thus obtained mixed solution can be used as a coating agent for modifying the surface of ophthalmic and medical devices. In the case of molding the mixed solution into molded articles suitable for various uses, a mold for molding suitable for a use can be used in, for example, the step b) among the following steps:

a) a step of obtaining a mixed solution comprising (meth) acrylated epsilon-polylysine of the present invention and the fore-mentioned other some monomer components, and a photo polymerization initiator and/or a thermal polymerization initiator;
  b) a step of introducing the mixed solution to a mold for molding;
  c) a step of obtaining an molding cured by irradiating UV light on and/or heating the mixed solution in the mold for molding;
  d) a step of demolding the molding;
  e) a step of removing an unreacted component from the molding; and
  f) a step of hydrating the molding.

The fore-mentioned mixed solution preferably comprises a water-soluble organic solvent for improving the uniformity of components in the polymerizable components. Specifically, an unreacted monomer can be diffused in the system to be participated in polymerization reaction even after proceeding of the polymerization reaction, by presenting a very slight amount of non-polymerizable organic solvent on the polymerizable components. That is, the residual polymerizable components can be reduced by using a water-soluble organic solvent.

Examples of the water-soluble organic solvent include alcohols having 1 to 4 carbons such as methanol, ethanol, 1-propanol and 2-propanol, or acetone, methylethylketone, dimethylformamide, dimethylsulfoxide, acetonitrile and N-methyl-2-pyrrolidone. As the organic solvent, a solvent capable of dissolving the polymerizable components used may be suitably selected to be used in accordance with the kind of the polymerizable components. Further, these may be used alone or a mixture of two or more of these compounds may be used.

The amount of the water-soluble organic solvent to be used in the mixed solution is preferably at most 5% by weight, more preferably 0.1 to 5% by weight and still more preferably 0.2 to 4% by weight. When the use amount is less than 0.1% by weight, the amount of the residual components at polymerization tends to be increased. On the other hand, when it exceeds 5% by weight, the mixed solution of the polymerizable components in which a diluent is added is heterogeneous, phase separation is generated at polymerization reaction which is carried out later, and the material obtained tends to become opaque.

Further, since the organic solvent used is soluble in water, it can be easily replaced with water at a step of elution treatment which is carried out later.

In a bulk polymerization process, since only the polymerizable components are mixed to be provided for polymerization, the viscosity of the system is extremely increased in accordance with proceeding of the polymerization, the components cannot be diffused in the highly viscous system, and a lot of monomers which cannot be participated in the polymerization reaction remain. In the production of medical devices, the elution treatment by water or the organic solvent is preferably carried out for reducing monomers remaining as low as possible.

An antimicrobial composition can also be obtained by a polymerization process by means of a molding method.

When the polymerizable components are heated to be polymerized by means of a molding method, the polymerizable component and a radical polymerization initiator are added in a mold corresponding to a desired shape, then the mold is gradually heated to carry out the polymerization of the polymerizable components, and mechanical process such as cutting process and polishing process is carried out on the molded article obtained if necessary.

Specific examples of the fore-mentioned radical polymerization initiator include, for example, 2,2'-azobisisobutyronitrile, 2,2'-azobis(2,4-dimethylvaleronitrile), benzoyl peroxide, t-butyl hydroperoxide, cumene hydroperoxide, lauroyl peroxide, t-butylperoxy hexanoate, 3,5,5-trimethylhexanoyl peroxide and the like. These can be used alone or a mixture of two or more of these compounds can be used. The amount of the radical polymerization initiator is about 0.001 to 2 parts based on 100 parts of the polymerizable components and preferably 0.01 to 1 part.

The heating temperature at heating the polymerizable components in a mold is at least 50° C. and preferably at least 60° C. from the viewpoints of shortening polymerization time and reducing the residual monomer components. Further, it is at most 150° C. and preferably at most 140° C. from the viewpoints of suppressing the volatilization of the respective polymerizable components and preventing the deformation of the mold. Further, the heating time at heating the polymerizable components in a mold is at least 10 minutes and preferably at least 20 minutes from the viewpoints of shortening polymerization time and reducing the residual monomer components. Further, it is at most 120 minutes and preferably at most 60 minutes from the viewpoint of preventing the deformation of the mold. The heating may be carried out by stepwise raising temperature.

When ultraviolet rays are irradiated on the polymerizable components to be polymerized by means of a molding method, the polymerizable component and a photopolymerization initiator are added in a mold corresponding to a desired shape, then ultraviolet rays are irradiated on the mold to carry out the polymerization of the polymerizable components, and mechanical process such as cutting process and polishing process is carried out on the molded article obtained if necessary. Irradiation with electron beam can be carried out in place of the irradiation of ultraviolet rays. In this case, the polymerizable components can be polymerized without a photo polymerization initiator. Further, the polymerization may be carried out, for example, by a bulk polymerization method and may be carried out by a solution polymerization method using a solvent and the like.

A material for the mold used in polymerization by the irradiation of ultraviolet rays is preferably general-purpose resins such as polypropylene, polystyrene, nylon and polyester which can transmit ultraviolet rays necessary for curing the material, and may be glass. These are molded and processed to prepare desired shapes. After the polymerizable components and the photo polymerization initiator, a pigment, a UV absorber and an organic diluent are mixed and added in a mold which corresponds to the shape of an ocular lens or do not correspond thereto, ultraviolet rays are irradiated on the mold to carry out polymerization of the polymerizable components. The wavelength range of UV irradiated can be selected in accordance with the function of the ocular lens material. However, the kind of the photo polymerization initiator used is required to be selected depending on the UV wavelength region irradiated.

The preferable irradiance of ultraviolet ray at irradiating ultraviolet ray on the polymerizable components in the mold is at least 1.0 mW/cm² for adequately curing the material and at most 50 mW/cm² for preventing the deterioration of the material. The irradiation time is preferably at least 1 minute for adequately curing the material. The irradiation with ultraviolet rays may be carried out at one step and ultraviolet rays with different intensity may be irradiated stepwise. Further, heating may be simultaneously carried out at irradiation of ultraviolet rays during polymerization and thereby the polymerization reaction is promoted and an ocular lens can be effectively molded.

The fore-mentioned heating temperature is preferably at least 25° C. from the viewpoint of promoting the reaction, more preferably at least 30° C. and further, preferably at most 100° C. from the viewpoint of suppressing the deformation of the mold, more preferably at most 90° C.

Specific examples of the fore-mentioned photo polymerization initiator include, for example, phosphine oxide type photo polymerization initiators such as 2,4,6-trimethylbenzoyl-diphenylphosphine oxide (TPO) and bis(2,4,6-trimethylbenzoyl)-phenylphosphine oxide; benzoin type photo polymerization initiators such as methyl orthobenzoylbenzoate, methyl benzoylformate, benzoin methyl ether, benzoin ethyl ether, benzoin isopropyl ether, benzoin isobutyl ether and benzoin n-butyl ether; phenone type photo polymerization initiators such as 2-hydroxy-2-methyl-1-phenylpropan-1-on, p-isopropyl-alpha-hydroxyisobutylphenone, p-t-butyl-trichloroacetophenone, 2,2-dimethoxy-2-phenylacetophenone, alpha, alpha-dichloro-4-phenoxyacetophenone and N,N-tetraethyl-4,4-diaminobenzophenone; 1-hydroxycyclohexyl phenyl ketone; 1-phenyl-1,2-propandione-2-(o-ethoxycarbonyl)oxime; thioxanthone type photo polymerization initiators such as 2-chlorothioxanthone and 2-methylthioxanthone; dibenzosuberone; 2-ethylanthraquinone; benzophenone acrylate; benzophenone; and benzyl. These may be used alone or a mixture of two or more of these compounds may be used.

Further, a photo sensitizer may be used together with the photo polymerization initiator. The contents of the photo polymerization initiator and photo sensitizer is about 0.001 to 2 parts based on 100 parts of the polymerizable components and preferably 0.01 to 1 part.

In an exemplary coating method, a desired ophthalmic or medical device is brought into contact with a mixed solution containing the (meth)acrylated epsilon-polylysine of the present invention, the hydrophilic monomer (B), the crosslinkable monomer (E), and an aqueous solvent, and irradiated with light (UV) and/or heated so that a desired coating can be formed on the surface. To form the coating efficiently, oxygen dissolved in the mixed solution is removed by irradiating the mixed solution in advance with ultrasonic waves or the like for degasification or bubbling an inert gas such as nitrogen gas to promote the polymerization reaction so that the coating can be applied more efficiently.

EXAMPLE

The following example specifically illustrates the present invention, but it should not be interpreted as limiting the scope of the invention.

1. Synthesis Example of (meth)acrylated epsilon-polylysine Macromonomer

Materials:

A (meth)acrylated polylysine macromonomer was synthesized by the scheme shown below using epsilon-polylysine with a number average molecular weight (Mn) of 3000 (manufactured by Handary Bio-Engineering), N,N'-dicyclohexylcarbodiimide (DCC (manufactured by Sigma-Aldrich)), N-hydroxysuccinimide (HoSu (manufactured by Sigma-Aldrich)), N,N-dimethylformamide (DMF (manufactured by Sigma-Aldrich)), and methacrylic acid (MA (manufactured by Sigma-Aldrich)).

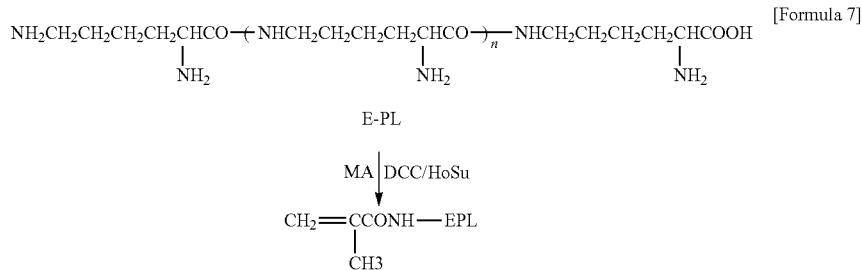

[Formula 7]

Detailed procedures including the amounts of each reagent used are as follows.

0.63 g (7.34 mmol) methacrylic acid and 0.93 g (8.1 mmol) N-hydroxy-succinimide were dissolved in 10 mL DMF and the solution was cooled to 0° C. To the solution, 1.51 g (7.34 mmol) DCC dissolved in 10 mL DMF was gradually added over 30 minutes, and the mixture was reacted with stirring at 0° C. for 2 hours, left to stand at room temperature for 4 hours, and then filtered. The resulting filtrate was added to 20 g (6.67 mmol) of an epsilon-polylysine solution (dissolved in a mixed solution of 200 ml water and 100 ml DMF) and stirred for 24 hours. After finishing the reaction, the solvent was removed, and a precipitate was produced in acetone and vacuum-dried overnight at 40° C. The dried precipitate was dissolved again in 100 mL of distilled water, and undissolved matters were removed by filtration, followed by precipitation and purification in 500 mL acetone and then overnight vacuum-drying at 40° C. The yield was greater than 80%.

2. NMR Measurement

Figure 1:
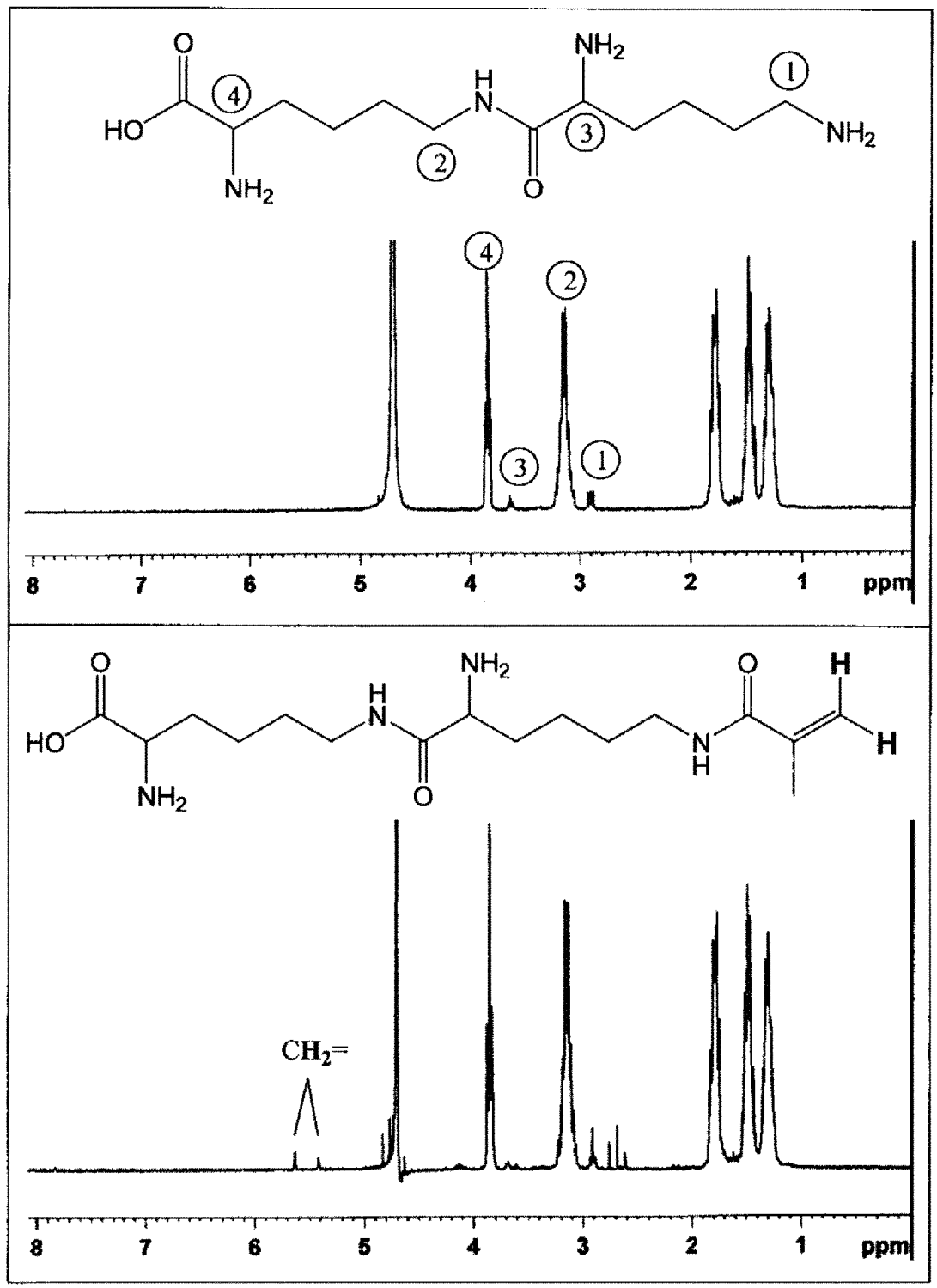
FIG. 1 shows the $^1$H NMR spectra of epsilon-polylysine (EPL: upper spectrum) and methacrylated epsilon-polylysine (MA-EPL: lower spectrum).

Production of (meth)acrylated epsilon-polylysine macromonomers and introduction of polymerization groups were examined by $^1$H NMR. For example, as shown in the NMR spectra in FIG. 1, the presence of a double bond of a methacrylic group can be observed at the positions of 5.4 ppm and 5.64 ppm; thus, the examination was conducted based on the presence or absence of a peak in these regions.

3. Measurement of Minimal Inhibitory Concentrations (MIC)

Minimal inhibitory concentrations (MIC) were determined by a standard microtiter dilution method in Mueller Hinton Broth (MHB) medium. Bacteria cells were grown overnight at 37° C. in MHB medium and diluted to a bacteria concentration of $10^6$ colony forming units (CFU)/ml. The bacteria concentration was adjusted to $5 \times 10^5$ CFU/ml by adding 100 µl of a suspension of the bacteria cultured under the above conditions to 100 µl of a polylysine aqueous solution diluted to $10^3$ to 1 µg/ml, and samples were prepared. The samples were incubated at 37° C. for 18 hours, and the MICs (lowest polylysine concentration that inhibited cell growth) after 18 hours were determined. Optical density measurement was carried out with an absorbance at a wavelength of 600 nm ($A_{600}$), and the MIC was defined as the lowest polylysine concentration that resulted in no bacterial growth after the 18-hour culture time. The results are shown in Table 1.

There was no significant difference in MIC between the synthesized polylysine macromer (hereinafter, the macromer is sometimes referred to as "MA-EPL") and the polylysine (EPL), which was a raw material.

TABLE 1

MIC comparison between EPL and MA-EPL (unit: µg/mL)

| | E. Coli | P. aeruginosa | S. aureus | S. marcescence | C. albicans | F. solani |
|---|---|---|---|---|---|---|
| EPL | 7.8 | 7.8 | 7.8 | 15.6 | 54 | 109 |
| MA-EPL | 7.8 | 7.8 | 15.6 | 15.6 | 27 | 54 |

4. Synthesis of Hydrogels

MA-epsilon-polylysine (0.1 g), N,N-dimethylacrylamide (DMA) (0.2 g), polyethylene glycol diacrylate (PEGDA) (0.1 g) (Mn=700, Sigma-Aldrich), water (3.6 ml), and a water soluble photo polymerization initiator (Irgacure 2959 (0.05%)) were mixed and stirred, and the mixed solution (10 wt %) was poured onto a horizontal glass plate. The solution was then exposed to UV light (365 nm, ±10 mW/cm², Osram 350-W mercury lamp manufactured by SUSS MicroTecG-mbH, model MA6) for 15 minutes to prepare hydrogels.

In the same manner, MA-EPL, DMA, PEGDA and polyethylene glycol monoacrylate (PEGA) (Mn=526, Sigma-Aldrich) were used to prepare four types of hydrogels (Samples A to D) by appropriately varying the monomer loadings.

5. Mechanical Properties

The Young's modulus and the strength of the samples were determined with an Instron tensile compression tester at a pressurization rate of 0.5 mm/sec using a cylindrical specimen with a diameter of 20 mm and a height of 10 mm.

Figure 2:
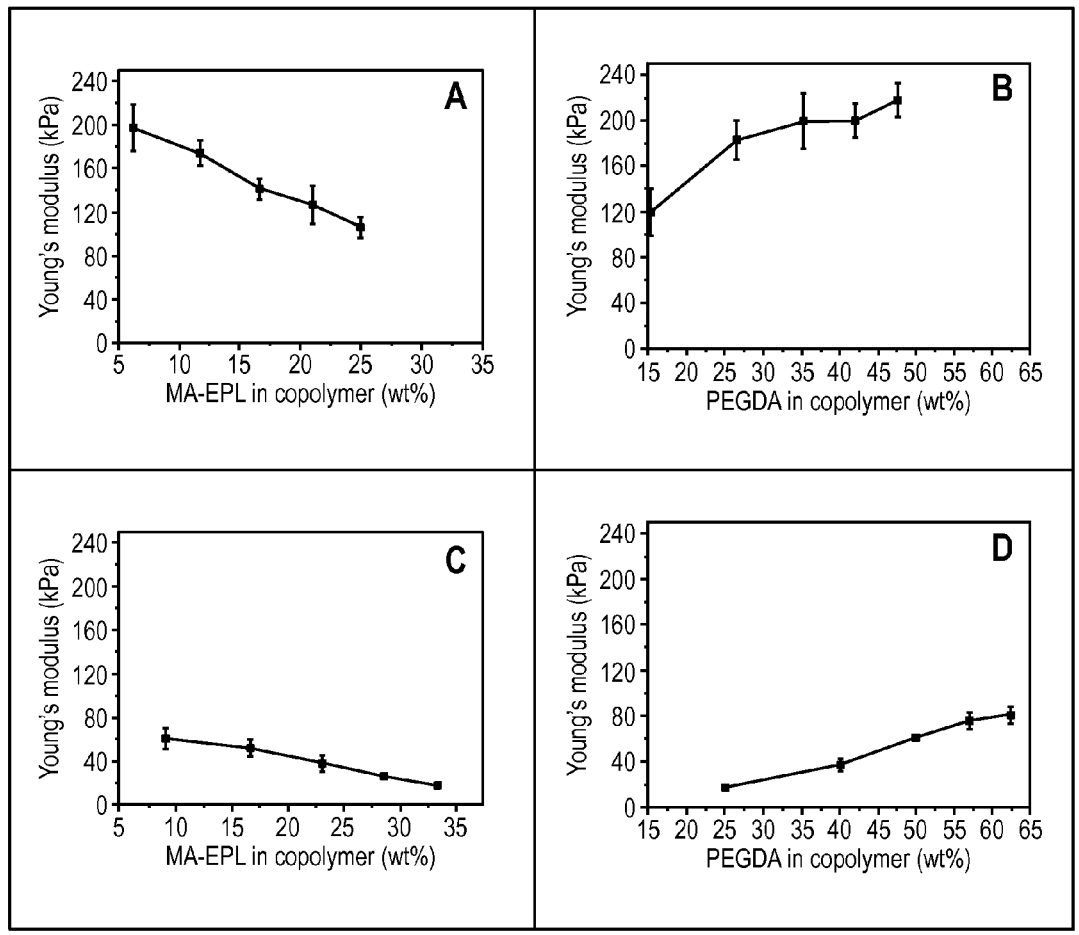
FIG. 2 shows the Young's moduli of hydrogels of the present invention prepared in the Examples. In this drawing, the vertical axis represents a Young's modulus, and the horizontal axis represents a percentage by weight of a component of interest in a copolymer.

The results are shown in FIGS. 2 and 3. It can be understood from FIG. 2 that increasing the amount of MA-EPL macromer tends to decrease the Young's modulus. In FIG. 2A, when the amount of MA-EPL was 6.25% by weight, the Young's modulus was 197 KPa.

6. Measurement of Water Absorption

The hydrogels that had been photo-crosslinked were immersed in a large amount of distilled water, and the weights at equilibrium swelling were measured at 25° C. Thereafter, the hydrogels were removed from the water and left to stand for 48 hours, and then the surfaces were wiped with water-absorbent papers and dried, followed by measurement of the dry weights. The water absorption was calculated by the following formula:

Water absorption=((hydrogel weight−dry weight)/dry weight)×100

The results are shown in FIG. 4. It can be understood that the amount of water absorption (water content) can be reduced by increasing the amount of the crosslinking agent (PEGDA).

7. Testing of Antimicrobial Properties of Polylysine Hydrogels

Polylysine hydrogel specimens were produced on culture polystyrene plates by the method described in the item 4 above, and the following antimicrobial testing was conducted. The compositions of the hydrogels were as follows.

Sample A1: Mix ratio of MA-EPL (6.25% by weight)-DMA (62.5% by weight)-PEGDA (31.25% by weight) (weight ratio of 1:10:5)

Sample A2: Mix ratio of MA-EPL (11.8% by weight)-DMA (58.8% by weight)-PEGDA (29.4% by weight) (weight ratio of 2:10:5)

Each polylysine hydrogel specimen was washed with distilled water for two days. Each bacterium was cultured for 24 hours on Trypticase Soy Agar, and then the cultured bacteria suspension was subjected to centrifugal suspension with a phosphate buffer (pH 7.2) three times. Ten microliters of each resulting bacteria suspension was inoculated to the center of the prepared polylysine hydrogel specimen, and maintained at 24° C. for 2 hours. Then, to determine the number of bacteria remaining in the bacteria suspension, specimens that were diluted 10-fold with a neutralizing agent were cultured in a Trypticase Soy Agar medium at 35° C. for 48 hours. Thereafter, the number of formed colonies was counted. The rate of reduction in the number of colonies was evaluated by the following formula:

LOG(reduction rate)=LOG(initial count of control)−
LOG(number of colonies after 2-hour contact)

The results are shown in Table 2. The hydrogels of the present invention exhibited excellent antimicrobial activity against all of *Escherichia coli, Pseudomonas aeruginosa, Serratia marcescens* (Serratia), *Staphylococcus aureus, Candida albicans* (*C. albicans*) and *Fusarium solani* (*F. solani*).

TABLE 2

| Microbe | Sample | Log (reduction rate) |
|---|---|---|
| E. coli | A1 | 2.77 |
| | A2 | 4.58 |
| P. aeruginosa | A1 | 2.44 |
| | A2 | 2.70 |
| S. marcescence | A1 | 3.88 |
| | A2 | 4.92 |
| S. aureus | A1 | 2.01 |
| | A2 | 2.42 |
| C. albicans | A1 | 0.98 |
| | A2 | 1.12 |
| F. solani | A1 | 1.55 |
| | A2 | 1.77 |

8. Examples of Coating Contact Lenses

A surface of a contact lens material disk comprising a fluoro alkyl(silicone-containing alkyl) fumarate copolymer was subjected to 13.56 MHz high-frequency induction plasma discharge (device type: March PX-500) at a power of 50 W for 1 minute by use of argon gas. After it was exposed to the atmosphere for 15 minutes, a 10% by weight aqueous solution of a coating composition (composition: 25% by weight of MA-EPL, 50% by weight of DMA, 25% by weight of PEGDA) prepared in advance was dropped onto the surface, covered with a polyester film (Melinex 453 manufactured by DuPont), and irradiated with UV (365 nm, 100 mW/cm$^2$, 30 minutes). The polyester film was removed, and the contact lens material disk was subjected to ultrasonic treatment overnight in deionized water to remove unreacted coating compositions. It was confirmed that a thin, colorless, transparent gel layer was uniformly grafted onto the entire surface of the resulting contact lens material disk.

This was colored with a fluorescent dye (fluoroscein), and it was confirmed that an epsilon-polylysine hydrogel layer was formed on the surface (see FIG. 5(I) showing photographs before the coating, and FIG. 5(II) showing photographs after the coating).

INDUSTRIAL APPLICABILITY

Due to high degree of biocompatibility, antimicrobial property and good wetting characteristics, the polymerizable composition and the antimicrobial composition of the present invention are widely used in many ophthalmic and medical devices, for example, biomedical devices such as contact lenses and bio-implants such as urinary catheters, pacemaker, heart valves, artificial heart, mammary prosthesis, intraocular lenses, wound dressings, artificial organs and delivery carriers for the bioactive agents, and total joint replacement.

What is claimed is:

1. A composition comprising epsilon-polylysine having (meth)acryloyl group, wherein the (meth)acryloyl group is attached to an amino group of the polylysine via an amide bond,
   wherein the composition comprises:
   (i) a hydrophilic monomer, wherein the hydrophilic monomer is selected from the group consisting of N-vinylpyrrolidone, hydroxyethyl (meth)acrylate, hydroxypropyl (meth)acrylate, hydroxybutyl (meth)acrylate, polyethyleneglycol mono(meth)acrylate, polypropyleneglycol mono(meth)acrylate, N,N-dimethylacrylamide (DMA), N,N-diethylacrylamide, N-(2-hydroxyethyl) acrylamide, N-isopropylacrylamide, acryloylmorpholine, 1-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, and 5-ethyl-3-methylene-2-pyrrolidone, and wherein the hydrophilic monomer can be used alone or two or more of these can be used in combination;
   and/or
   (ii) a crosslinkable monomer, wherein the crosslinkable monomer is selected from the group consisting of allyl (meth)acrylate, vinyl(meth)acrylate, 4-vinylbenzyl (meth)acrylate, 3-vinylbenzyl(meth)acrylate, methacryloyloxyethyl acrylate, ethyleneglycol di(meth)acrylate, diethyleneglycol di(meth)acrylate, diethyleneglycol diallyl ether, polyethyleneglycol di(meth)acrylate, polypropyleneglycol di(meth)acrylate, butanediol dimethacrylate, and trimethylolpropane trimethacrylate, and wherein the crosslinkable monomer can be used alone or a mixture of two or more of these compounds can be used.

2. The composition of claim 1, wherein the epsilon-polylysine having (meth)acryloyl group is polymerizable.

3. The composition of claim 1, wherein the content of the epsilon-polylysine having (meth)acryloyl group is about 0.1 to 99% by weight based on the whole amount of the composition.

4. The composition of claim 2, wherein the composition is a coating agent for ophthalmic or medical use.

5. The composition of claim 2, wherein the composition is antimicrobial.

6. The composition of claim 3, wherein the composition is a coating agent for ophthalmic or medical use.

7. The composition of claim 3, wherein the composition is antimicrobial.

8. An ophthalmic or medical device comprising the antimicrobial composition of claim 5.

9. The device of claim 8, wherein the device is a contact lens.

10. A composition comprising epsilon-polylysine having (meth)acryloyl group, wherein the (meth)acryloyl group is attached to an amino group of the polylysine via an amide bond, wherein the epsilon-polylysine having (meth)acryloyl group is polymerizable, and wherein the composition is a coating agent for ophthalmic or medical use.

11. The composition of claim 10, wherein the content of the epsilon-polylysine having (meth)acryloyl group is about 0.1 to 99% by weight based on the whole amount of the composition.

12. An ophthalmic or medical device comprising an antimicrobial composition, the composition comprising epsilon-polylysine having (meth)acryloyl group, wherein the (meth)acryloyl group is attached to an amino group of the polylysine via an amide bond, and wherein the epsilon-polylysine having (meth)acryloyl group is polymerizable.

13. The device of claim 12, wherein the device is a contact lens.

* * * * *